(12) United States Patent
Jenkin

(10) Patent No.: US 9,603,737 B2
(45) Date of Patent: Mar. 28, 2017

(54) PORTABLE URINAL SYSTEMS AND METHODS OF COLLECTING URINE

(71) Applicant: Brian Jenkin, Portland, OR (US)

(72) Inventor: Brian Jenkin, Portland, OR (US)

(*) Notice: Subject to any disclaimer, the term of this patent is extended or adjusted under 35 U.S.C. 154(b) by 263 days.

(21) Appl. No.: 14/508,546

(22) Filed: Oct. 7, 2014

(65) Prior Publication Data

US 2016/0095479 A1 Apr. 7, 2016

(51) Int. Cl.
*A47K 11/12* (2006.01)
*A61F 5/453* (2006.01)
*B60R 15/04* (2006.01)

(52) U.S. Cl.
CPC .............. *A61F 5/453* (2013.01); *A47K 11/12* (2013.01); *B60R 15/04* (2013.01)

(58) Field of Classification Search
CPC ......... A47K 11/12; A61F 5/453; A61F 5/455; A61F 5/4556; B60R 15/04; A61G 9/006
USPC ..................................... 4/144.1–144.4, 114.1
See application file for complete search history.

(56) References Cited

U.S. PATENT DOCUMENTS

| | | | | |
|---|---|---|---|---|
| 2,379,346 A | * | 6/1945 | Farrell | A61F 5/453 604/351 |
| 2,745,111 A | * | 5/1956 | Podmorski | A61F 5/4405 141/297 |
| 5,010,599 A | * | 4/1991 | Nilsson | A61F 5/44 4/144.2 |
| 5,551,097 A | * | 9/1996 | Short | A61G 9/006 4/144.1 |
| 5,797,147 A | * | 8/1998 | Young | A47K 11/12 137/515 |
| 5,848,443 A | | 12/1998 | Waugh | |
| 5,946,742 A | | 9/1999 | Parker | |
| 6,968,577 B1 | * | 11/2005 | Taft, Jr. | A47K 11/12 4/144.1 |
| 8,181,284 B1 | | 5/2012 | Parker | |
| 8,650,669 B1 | | 2/2014 | Kolter | |
| 2003/0140409 A1 | | 7/2003 | Johnson | |
| 2006/0277670 A1 | * | 12/2006 | Baker | A61G 9/006 4/144.1 |
| 2008/0163411 A1 | | 7/2008 | Brown | |
| 2009/0249532 A1 | * | 10/2009 | Smith | B60R 15/04 4/114.1 |

* cited by examiner

*Primary Examiner* — J. Casimer Jacyna
(74) *Attorney, Agent, or Firm* — Baumgartner Patent Law; Marc Baumgartner

(57) ABSTRACT

A portable urinal system including a handheld urinal and a reservoir. The handheld urinal has a neck assembly, with a user operated neck valve assembly permitting urine to flow through the neck assembly, and a urinal cup coupled to the neck assembly so that upon use of the urinal and operation of the neck valve assembly by the user, urine flows through the neck assembly into the urinal cup. The reservoir has a larger volume than the urinal cup and includes a lid assembly with a substantially rigid spout assembly and a reservoir cup. Urine is transferred from the urinal to the reservoir when the user couples the urinal cup to the spout assembly and opens the spout assembly such that urine collected in the urinal cup drains into the reservoir cup.

19 Claims, 11 Drawing Sheets

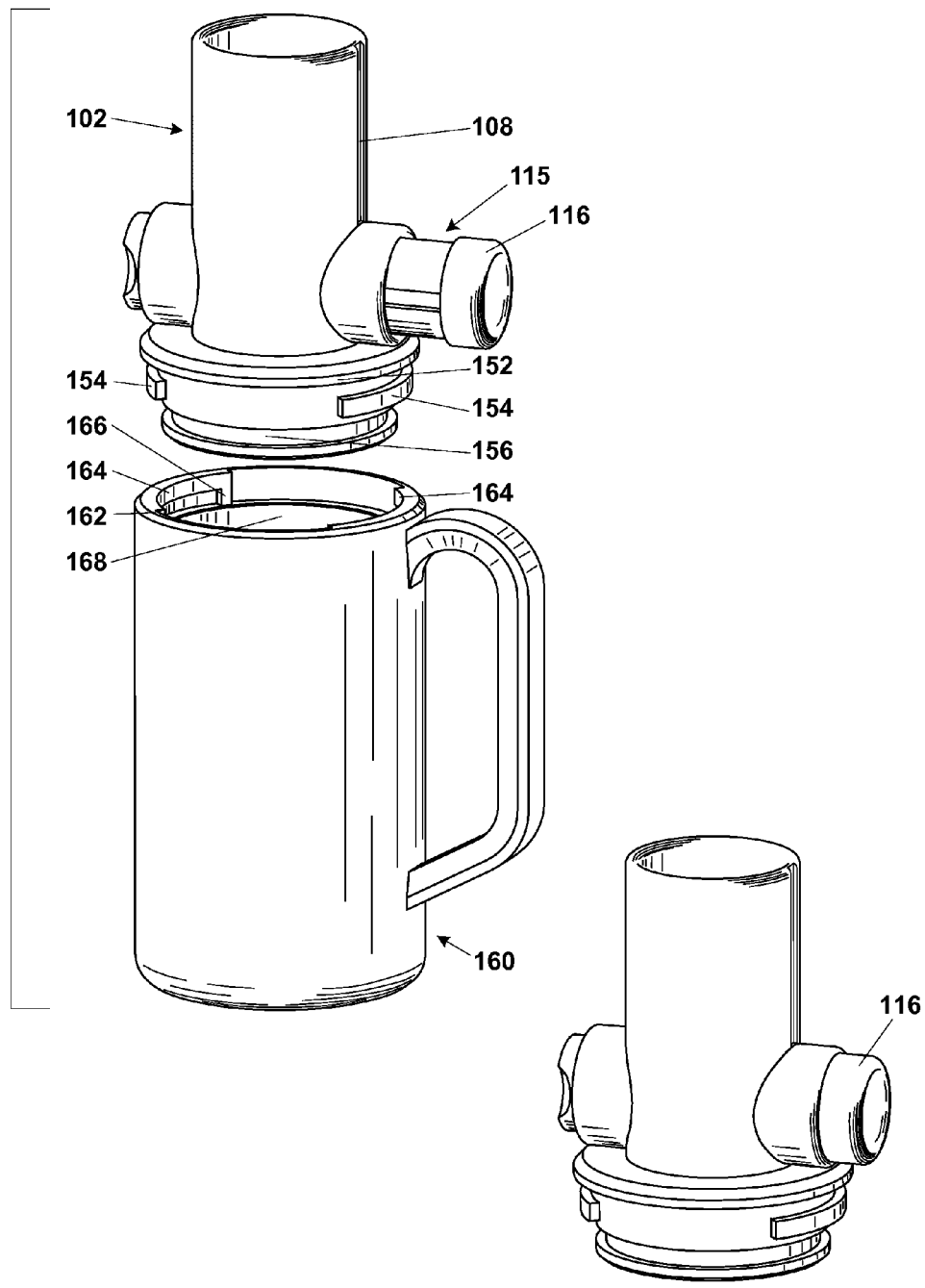

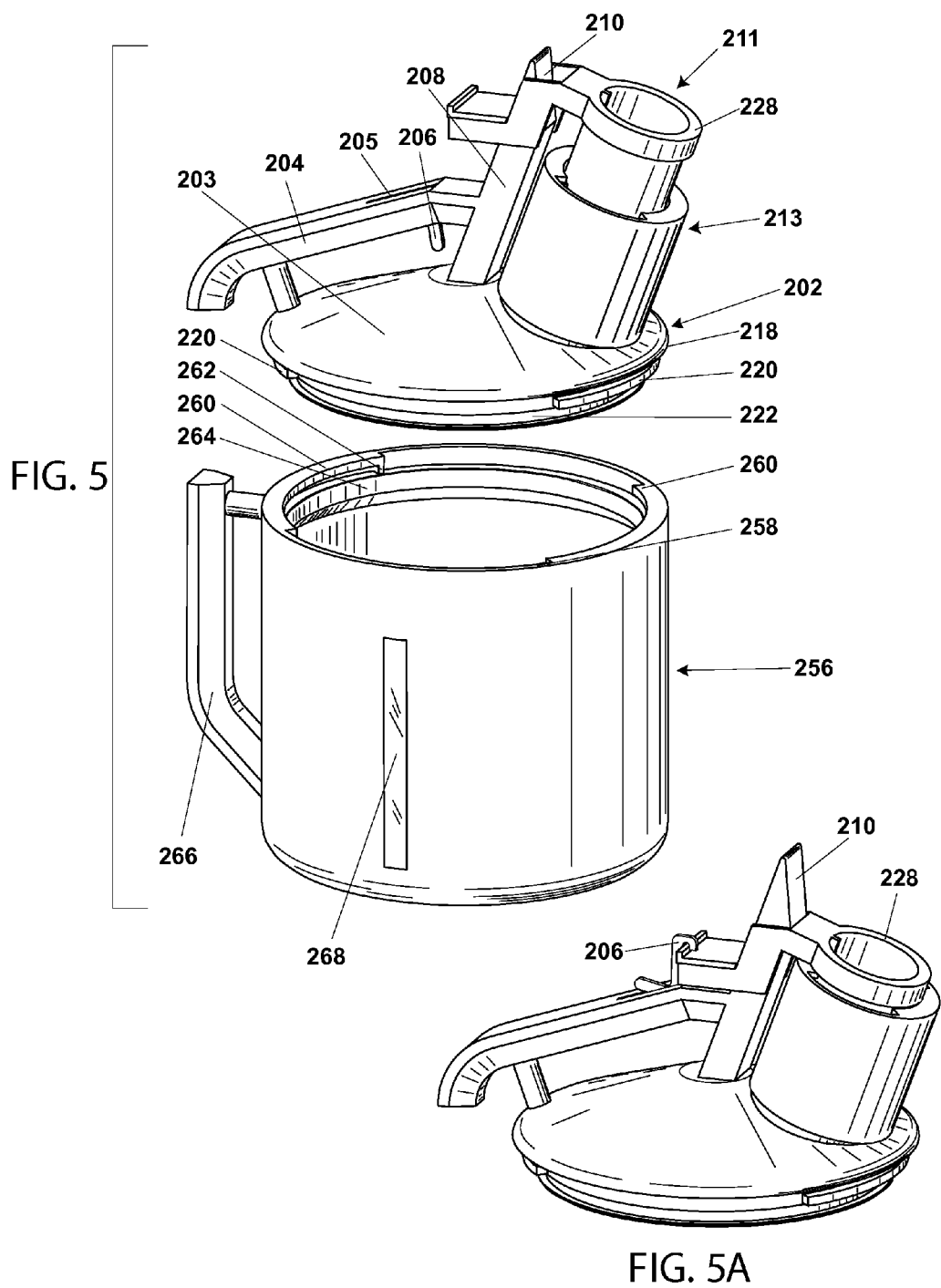

PORTABLE URINAL SYSTEMS AND METHODS OF COLLECTING URINE

BACKGROUND

The present disclosure relates generally to portable urinal systems and methods of collecting urine. In particular, systems and methods including a handheld urinal and a separate collection reservoir are described.

For a long-haul truck driver who is on the road, access to a convenient restroom facility is generally not available when the need to urinate arises. In such situations, the first task is to get the vehicle safely parked alongside the road. The driver will then relieve him/herself, and up until now, the two most common options have been either to step outside the vehicle or to use some sort of ad-hoc container as a urinal. This scenario, repeated thousands of times on a daily basis, carries many undesirable aspects.

To begin with, just finding a safe place to park can take some time, and during that interval, the increasing need for relief introduces a level of distraction that can seriously endanger both the driver and other nearby vehicles. Once parked, exiting the cab not only exposes the driver to the risk of bodily harm from other vehicles, but if at night and/or in a remote location, the security of the driver, the rig, and the cargo may all be seriously compromised. Outside urination not only casts the entire trucking industry in a negative light, but with current public concern for the environment, drivers who use this option will increasingly find themselves in legal trouble.

For the driver who prefers to stay in the cab, there are very few satisfactory options. Currently there is virtually no commercially available product specifically designed as a urinal to be used in the cab. A few products claim to serve this purpose, but none of them appear to be very practical solutions. There is a group patents including U.S. Pat. No. 8,181,284, U.S. Pat. No. 5,551,097. US20030140409, and US20080163411 that are apparently designed for the trucking industry. A common design characteristic is that they all incorporate a receiver (funnel, catheter) that is connected to the reservoir via a flexible hose. There are several practical drawbacks to the use of a hose—e.g. incompatibility with the day-to-day activities in the sleeper cab space, increased points of possible leakage, and greater difficulty in maintaining the overall hygiene of the system. It also appears that the implementation of all of these designs requires permanent modifications to the sleeper cab—something not tolerated by most trucking companies.

A web search yields references to the PIT STOP® and to the GOPILOT®. Neither of these would require cab modification, but similar to the previous group, each of these incorporates a receiver-hose-reservoir design. The GOPILOT® system appears to only have a capacity of only 1 gallon, and it's not seen as particularly useful to the average trucker. See also U.S. Pat. No. 8,650,669, which appears to describe the GOPILOT® system.

The teachings herein, which are directed to the concept of two distinctly separate containers (Urinal and Reservoir) has not been seen before. To the objectives of hygiene, convenience, security, and simplicity, the embodiments disclosed herein are a major departure from all of the other applicable prior art.

In the absence of any viable alternatives, the container of choice is usually a plastic beverage container of 1-4 liter capacity. Because they were never designed for this purpose, there are several ways in which such containers are very subject to spillage. Also because they are often used to accumulate urine over a period of several days, they are vulnerable to the build-up of odor and infectious bacteria levels. Since there is no generally acceptable means for disposal, these containers are often discarded along highway shoulders, and known to the general public as "truck bombs."

The current situation can also result in negative health impacts. Frequent prolonged periods of having to "hold it" are known to increase the likelihood of bladder and kidney disorders. Also in order to avoid the previously described situations, drivers will often minimize liquid intake and thereby incur problems associated with inadequate hydration.

SUMMARY

The portable urinal systems and methods of collecting urine described herein were conceived as a solution to many of these issues. As disclosed herein, portable urinal systems are described consisting of two separate receptacles, these being a hand-held urinal and a reservoir.

At time of use, urine is discharged into the handheld urinal, and once that discharge is completed, a fail-safe valve in the urinal neck will prevent accidental spillage of the contents.

Immediately after discharge, or at some later convenient time, the content of the handheld urinal is drained into the reservoir through a coupling system that is uniquely designed to prevent spillage while the liquid is being transferred. Once the transfer is complete, the handheld urinal and the reservoir spout can be easily cleaned with the use of commonly available sanitary wipes, household disinfectants, and/or paper towels. The reservoir spout includes a fail-safe valve that prevents accidental spillage of the stored contents and also seals in odor and bacteria.

This Summary is submitted with the understanding that it is not be used to interpret or limit the scope or meaning of the claims. Further, the Summary is not intended to identify key features or essential features of the claimed subject matter, nor is it intended to be used as an aid in determining the scope of the claimed subject matter.

BRIEF DESCRIPTION OF THE DRAWINGS

FIG. 3 is an exploded perspective view of the handheld urinal shown in FIG. 1 with the neck assembly detached from the urinal cup and showing the valve plunger in a closed position.

FIG. 3A is a perspective view of the neck assembly showing the valve plunger in the open position.

FIG. 5 is an exploded perspective view of the reservoir shown in FIG. 2 with the lid assembly detached from the reservoir cup and showing the spout valve assembly in a closed position.

FIG. 5A is a perspective view of the spout valve assembly showing the lid assembly in an open position.

DETAILED DESCRIPTION

Figure 1:
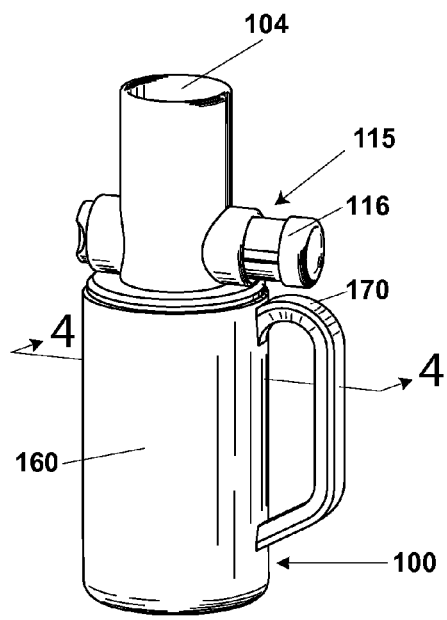
FIG. 1 is a perspective view of an example of a handheld urinal.

The disclosed systems and methods will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Representative embodiments according to the inventive subject matter are shown in FIGS. 1-10, wherein the same or generally similar features share common reference numerals.

The portable urinal systems described herein include a handheld urinal and reservoir as two stand-alone containers that can be easily coupled with each other. Urine is transferred from the urinal into the reservoir when the user couples the urinal to reservoir.

The design of urinal and reservoir as separate receptacles provides several advantages. For example, since urinary discharge is into the urinal, and not directly into the reservoir, the reservoir can have a relatively large capacity, and can be located in a secure out-of-the-way place, needing to be moved only when it is to be emptied. The relatively small (single use) capacity of the urinal enhances its portability, and permits its use while standing, kneeling, or sitting, and while in any part of the vehicle's sleeper cab.

If urination is necessary during a sleep period, use of the urinal eliminates the need to exit the cab and minimizes interruption to the driver's sleep pattern. This aspect is significant because of the known relationship between quality of sleep and safe operation of the vehicle.

Another advantage of the two part design is that no part of the body ever needs to come in contact with or be in close proximity to any bacteria associated with the accumulated contents of the reservoir. Furthermore, the levels of odor and bacteria in the reservoir may be minimized with the use of a miniature "urinal biscuit" inside the reservoir cup.

The disclosed systems allow a quick and complete disassembly and re-assembly of the urinal and reservoir for purposes of cleaning. For example, the routine of a typical long-haul driver includes use of a truck stop shower facility every 2-3 days. On such occasions, the system can be completely disassembled, and with all parts contained within the reservoir cup, for example, they can be thoroughly cleaned and rinsed while in the shower.

Although the disclosed systems were developed with over-the-road truckers in mind, they may also be applicable to the needs of utility, construction, and emergency crews who must frequently work in remote locations. In fact, they are of use to both workers and recreationalists in any situation that does not permit easy access to permanent restroom facilities for an extended period of time, and that requires a secure, sanitary, and convenient alternative.

Figure 2:
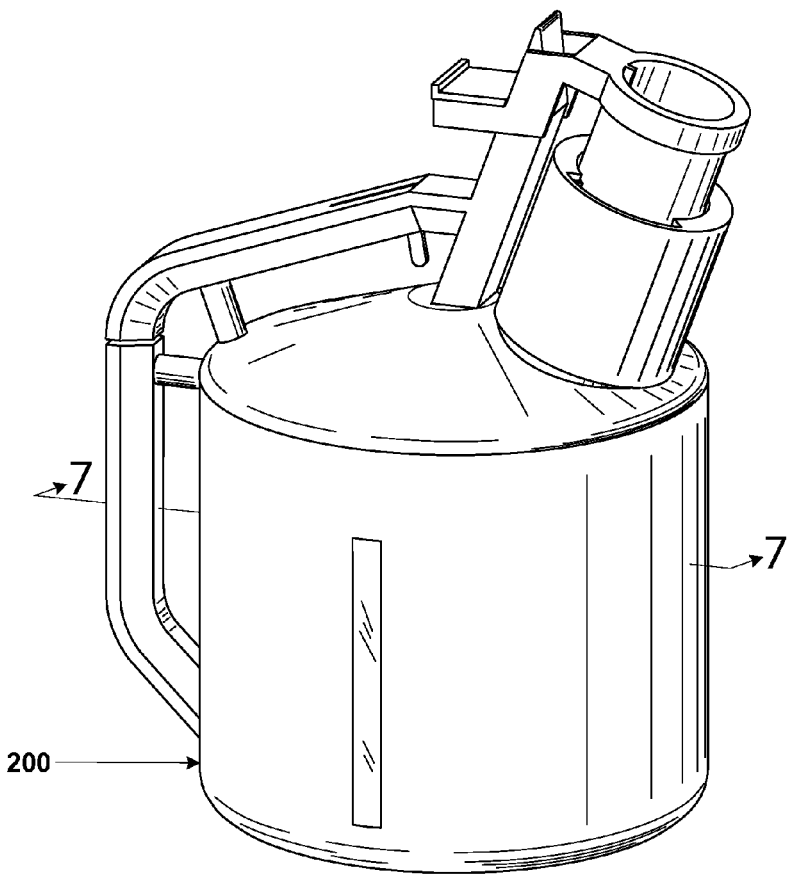
FIG. 2 is a perspective view of an example of a reservoir.
Figure 8:
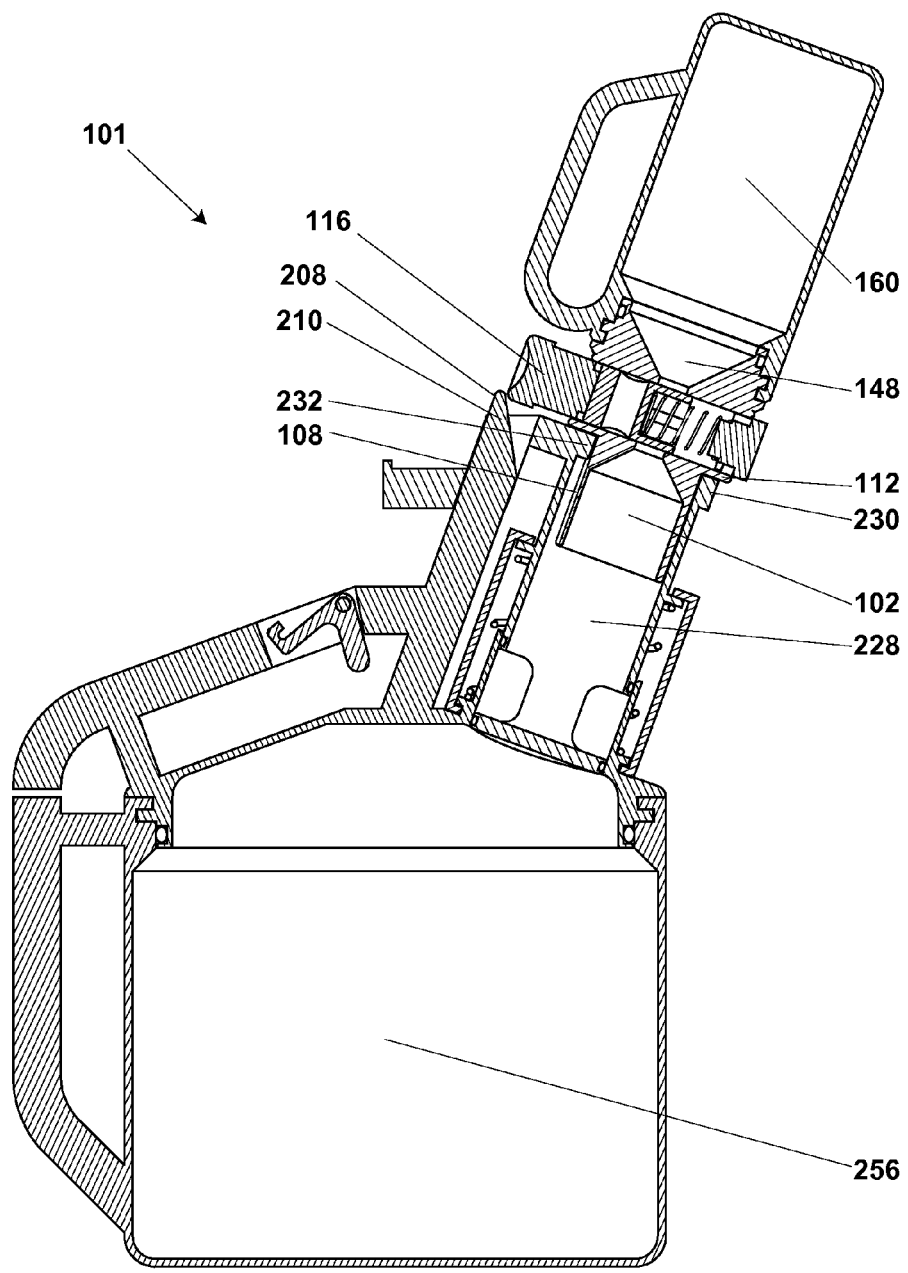
FIG. 8 is a cross-sectional side view of the portable urinal system with the handheld urinal coupled to the reservoir and showing the neck valve assembly and the spout valve assembly in closed positions.
Figure 8A:
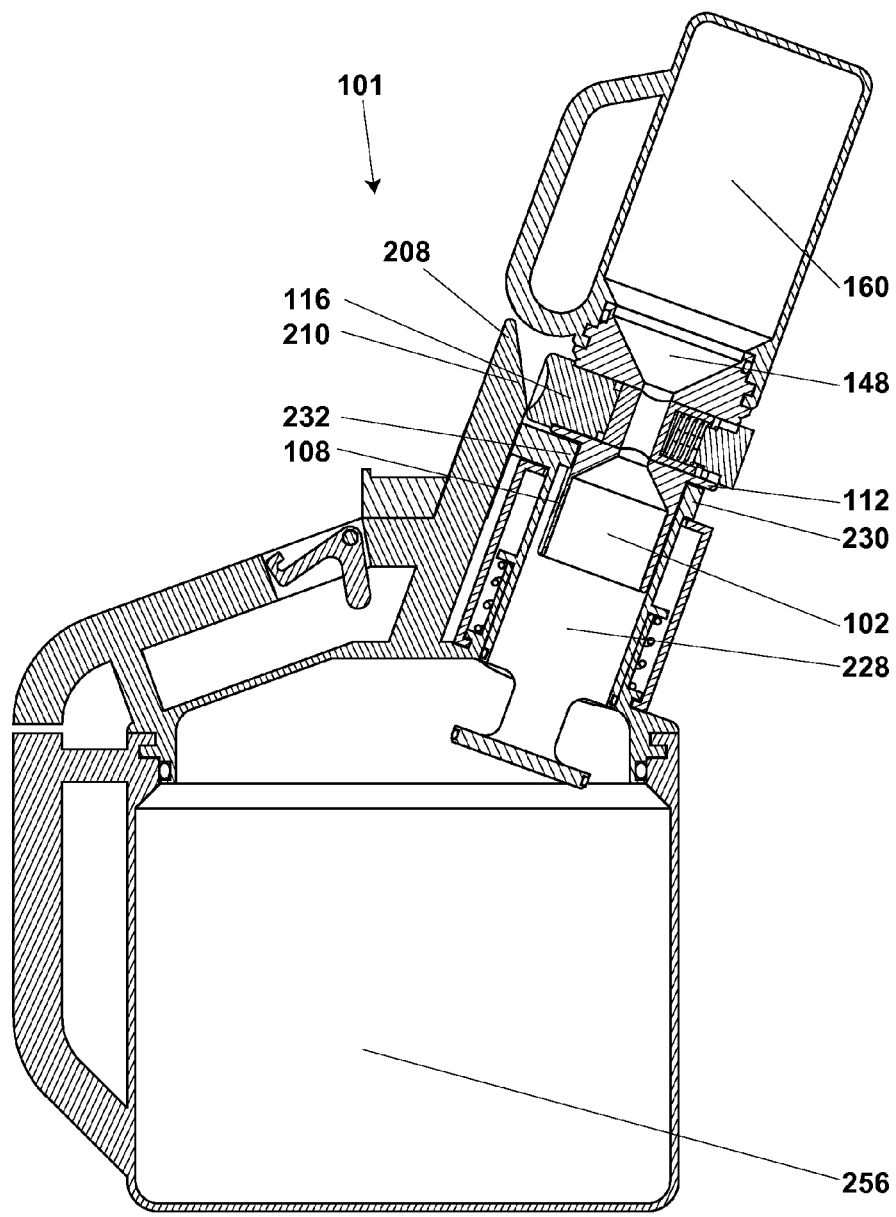
FIG. 8A is a cross-sectional side view of the portable urinal system with the handheld urinal coupled to the reservoir and showing the neck valve assembly and the spout valve assembly in open positions.

FIGS. 8 and 8A shows a portable urinal system 101 that consists of a handheld urinal 100 and a reservoir 200. FIGS. 1 and 2 convey relative sizes of an example embodiment of the portable urinal system. Reservoir 200 has a larger volume than urinal cup 100.

In the embodiment shown, approximate capacities of the handheld urinal and the reservoir are about 500 ml and about 6 liters respectively, therefore the reservoir can be expected to accommodate about 12-24 uses of the urinal, for example over a period of 2-5 days. This gives the typical truck driver enough opportunity to encounter a permanent restroom facility, at which time the reservoir contents can be conveniently, safely, and discreetly disposed of.

In some embodiments, the urinal is sized in volume to receive about 400 to about 600 ml of urine, and the reservoir is sized in volume to store at least about 1600 to about 6000 ml of urine.

Although the embodiments described herein show many of the system's parts having a cylindrical shape, and all references to rotational movement of those parts are relative to their respective cylindrical axes, other embodiments may include different shapes, for example, in some embodiments a cuboid shape for the reservoir cup may be desired.

Handheld urinal 100 has a neck assembly 102 and a urinal cup 160, detachable from each other as shown in FIG. 3. Neck assembly 102 includes a user operated neck valve assembly 115 that is adjustable between open and closed positions. Neck valve assembly 115 is formed of a sleeve 112 and a valve plunger 116. In FIG. 3, the valve plunger 116 is in the valve-closed (normal) position, while FIG. 3A shows the plunger in the valve-open (in use) position. Although, parts of the neck assembly allow repositioning between open and closed positions, the neck assembly is formed as a substantially rigid construction, without corrugated connections or flexible tubing.

Figure 3B:
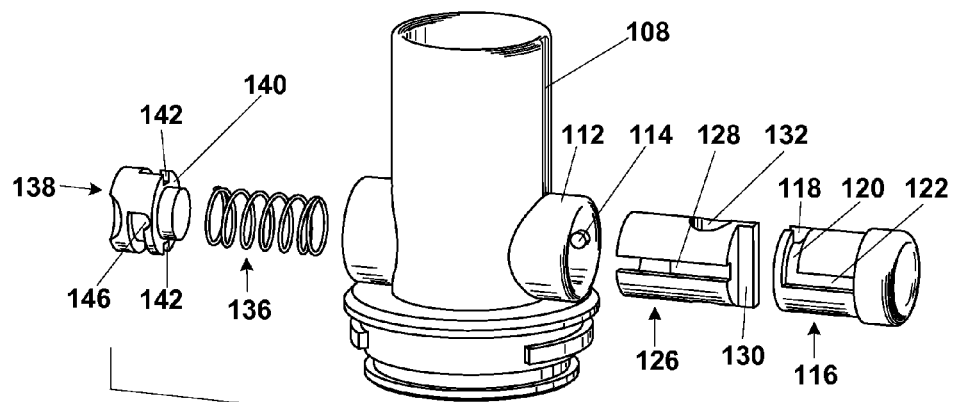
FIG. 3B is an exploded perspective view of the front side of the neck assembly of the handheld urinal of FIG. 1.
Figure 3C:
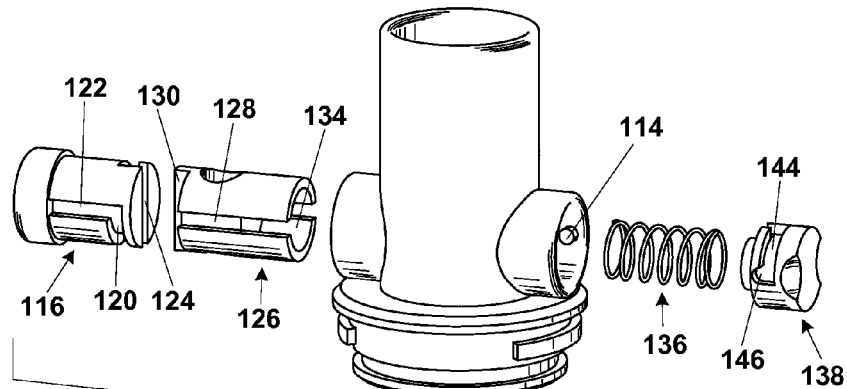
FIG. 3C is an exploded perspective view of the back side of the neck assembly of the handheld urinal of FIG. 1.
Figure 4:
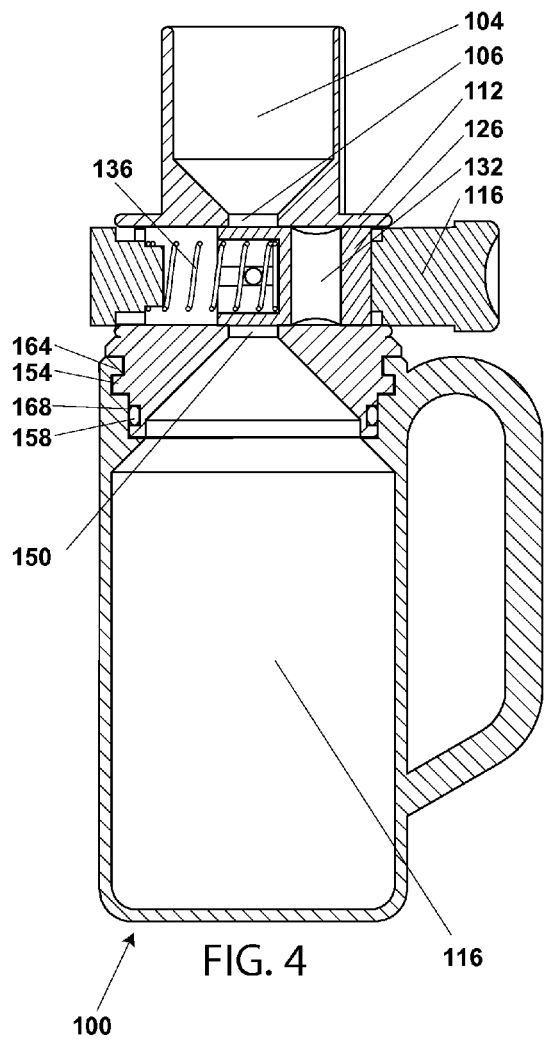
FIG. 4 is a cross-sectional side view of the handheld urinal shown in FIG. 1 with the neck valve assembly in a closed position.
Figure 4A:
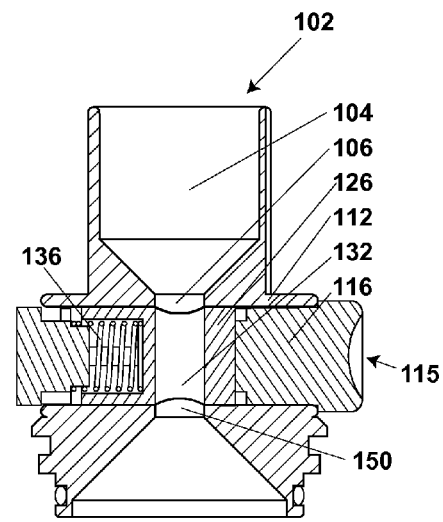
FIG. 4A is a cross-sectional side view of the neck assembly with the neck valve assembly in a open position.
Figure 4B:
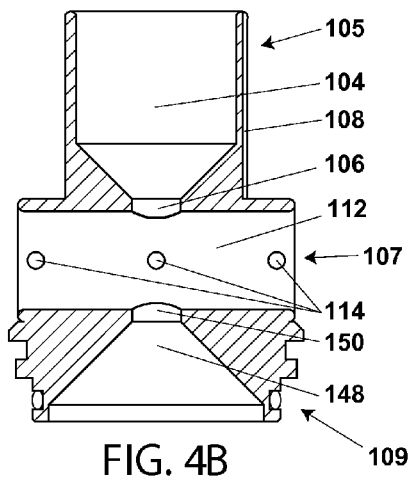
FIG. 4B is a cross-sectional side view of the neck assembly without the neck valve assembly inserted.

Cross-sectional views of the urinal are shown in FIGS. 4, 4A, and 4B. As shown in FIG. 4B, the shell of the urinal neck is an integrated assembly consisting of three sections. The upper section 105 is configured to receive urine from the urethral opening of the user. Upper section 105 incorporates an inlet funnel 104 and, on the outside of the funnel 104, the lateral guide groove 108 (also shown in FIG. 3). The lower section 109 has an outlet, such as an outlet funnel 148, and a plurality of coupling elements such as ribs 154 and 164 discussed below. Molded into the middle section 107 of the neck is the cylindrical sleeve 112 which houses the components of a sliding plug valve.

Along each side of the inner valve sleeve are three guide pins 114 positioned as shown. Also between the two funnel sections 104, 148 and the valve sleeve 112 are flow ports 106 and 150 that align with plug port 132.

As shown in FIGS. 3 and 4, neck assembly 102 has coupling elements, for example two interlock ribs 154 which are positioned 180° apart around the base of the neck. Urinal cup 160 has two complementary coupling elements, for example two interlock ribs 164 and two interlock rib stops 166 which are positioned 180° apart inside the rim of cup 160.

The O-ring groove 156 retains an O-ring 158 which, as shown in FIG. 4, forms a seal with the cup inner face 168. This seal prevents leakage between the neck and cup whenever the urinal is up-ended. In other embodiments, a seal between the neck assembly and urinal cup may be accomplished by other suitable means, for example by placing compression seals between mating horizontal surfaces of the neck assembly and urinal cup.

FIG. 4 also shows how neck assembly 102 and urinal cup ribs 154 and 164 interlock with each other when the neck is secured to cup 160. In other embodiments, the neck assembly and urinal cup can be secured by any other suitable fastening means, for example screws.

FIGS. 3B and 3C are exploded views of the urinal neck assembly showing the sliding valve components. The two views are oriented respectively to opposite ends of the valve sleeve 112. A valve plug 126 slides back and forth in the sleeve between the valve-open and valve-closed positions. In the valve-open position, plug port 132 is aligned with funnel ports 106 and 150 (FIG. 4A). In the closed position (FIG. 4), plug port 132 is offset from the funnel ports 106, 150 and flow between them is blocked by the solid portion of the plug. On each side of said plug are lateral guide grooves 128 which engage guide pins 114, and thereby prevent rotation of plug 126 as it moves back and forth in sleeve 112.

Valve plug 126 is held in the valve-closed position by pressure from spring 136. One end of spring 136 seats against plug 126 in recess 134, and the other end seats against shoulder 140 of the spring retainer cap 138. Retainer cap 138 incorporates two symmetrical (about the cap axis) sets of grooves 142, 144, and 146 which engage two guide pins 114 positioned near the end of valve sleeve 112. Valve plunger 116 also incorporates two symmetrical (about the plunger axis) sets of grooves 118, 120, and 122, which engage the two guide pins 114 positioned near the other end of valve sleeve 112. The interior face of valve plunger 116 incorporates a vertical groove 124 which interlocks with vertical key 130 on the matching end face of valve plug 126.

With the valve fully assembled, the pressure of spring 136 against retainer cap 138 will seat the sleeve-end guide pins 114 into detent grooves 146 of retainer cap 138. The spring pressure against plug 126 also forces key 130 into groove 124. Without these features, the plunger and/or the valve cap could be subject to inadvertent rotation resulting in accidental disassembly of the valve. In order for the urinal/reservoir coupling mechanism (as described below) to work correctly, the neck valve is assembled so that the plunger 116 is inserted into valve sleeve 112 end that is adjacent to guide groove 108.

Portable urinal system 101 also includes a reservoir 200 having a larger volume than handheld urinal 100. Reservoir 200 has a lid assembly 202 and a reservoir cup 256, detachable from each other as shown in FIG. 5. Lid assembly 202 includes a substantially rigid spout assembly 213 configured to releasably couple to neck assembly 102 of urinal 100. Reservoir cup 256 is configured to store urine received from urinal 100 via spout assembly 213. Urine is transferred from urinal 100 to reservoir 200 when the user couples urinal neck assembly 102 to spout valve tube 228 such that both the urinal neck valve and the reservoir spout valve open simultaneously causing urine collected in urinal cup 160 to drain into reservoir cup 256.

Lid assembly 202 further has a lid cover 203 that is integrated with a handle 204 and spout assembly 213. Spout assembly includes an engaging element that engages a portion of the neck valve assembly, such as valve plunger 116. FIGS. 8 and 8A illustrate how valve plunger 116 is being operated via an engaging element, for example guide pillar 208. When pressure is applied to the handheld urinal, i.e., the urinal is being pushed downward towards the reservoir cup by the user, both the neck valve assembly and spout valve assembly move to their open positions. The shape of guide pillar 208 includes the wedge face 210, the function of which is described below.

Figure 7:
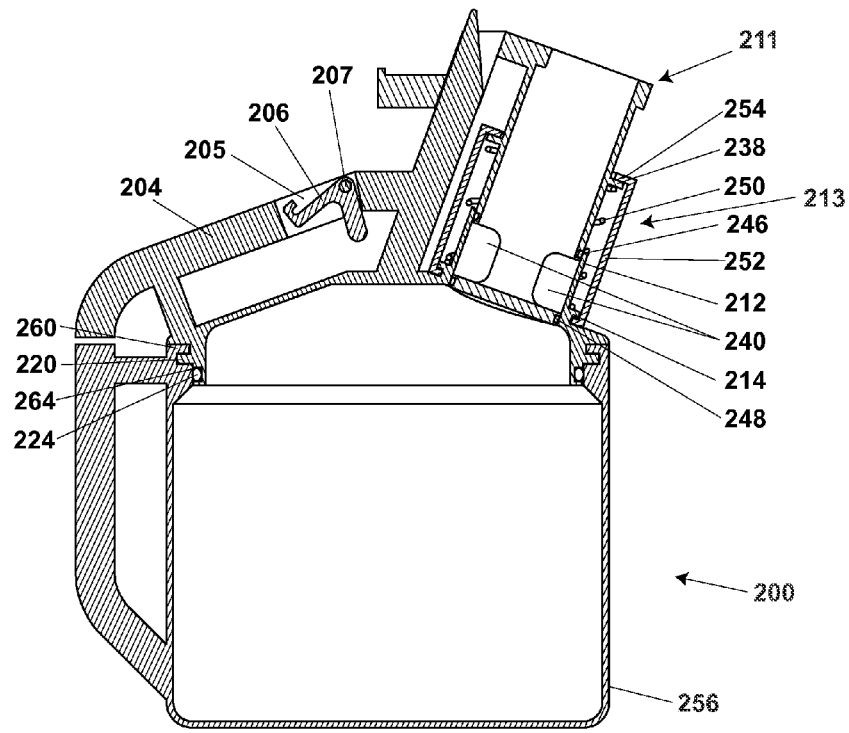
FIG. 7 is a cross-sectional side view of the reservoir showing the spout valve assembly in a closed position.
Figure 7A:
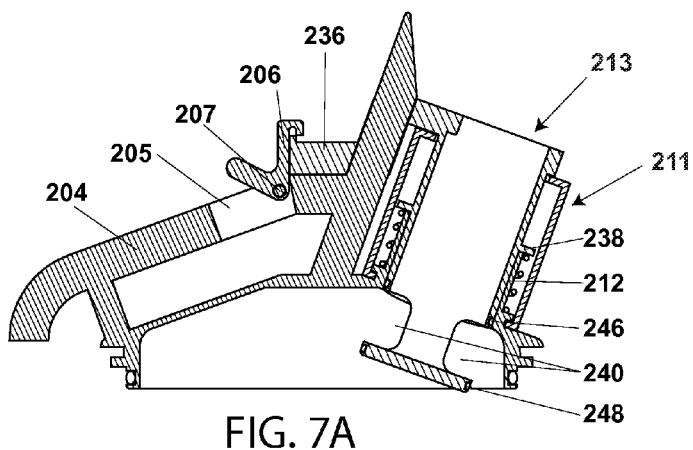
FIG. 7A is a cross-sectional side view of a section of the reservoir showing the spout valve assembly in an open position.

The handle includes a latch 206 which, as shown in cross-sectional FIGS. 7 and 7A, is built into recess slot 205, and rotates about pin 207 from the position shown in FIG. 7 to that shown in FIG. 7A.

Lid cover 203 also incorporates a substantially rigid spout assembly 213 and a substantially rigid spout valve assembly 211. The lid assembly provides for coupling to the urinal neck assembly without corrugated connections or flexible tubing. Spout assembly 213 and spout valve assembly 211 are moveable relative to each other to operate the lid assembly between open and closed positions. FIG. 5 shows spout valve assembly 211 having tube 228 in the valve-closed (normal) position, while FIG. 5A shows tube 228 in the valve-open (in use) position.

As shown in FIG. 5, construction of lid cover 203 includes two interlock ribs 220 which are positioned 180° apart around the base of the lid. Construction of reservoir cup 256 includes a handle 266 and a transparent sight glass 268. It also includes coupling elements in the form of two interlock ribs 260 and two interlock rib stops 262 which are positioned 180° apart inside the rim of reservoir cup 256. The O-ring groove 222 retains an O-ring 224 which, as shown in FIG. 7, forms a seal with the cup inner face 264. This seal prevents leakage between lid assembly 202 and reservoir cup 256 whenever the reservoir is up-ended. FIG. 7 also shows how ribs 220 and 260 interleave with each other when the lid is secured to the cup.

Figure 6:
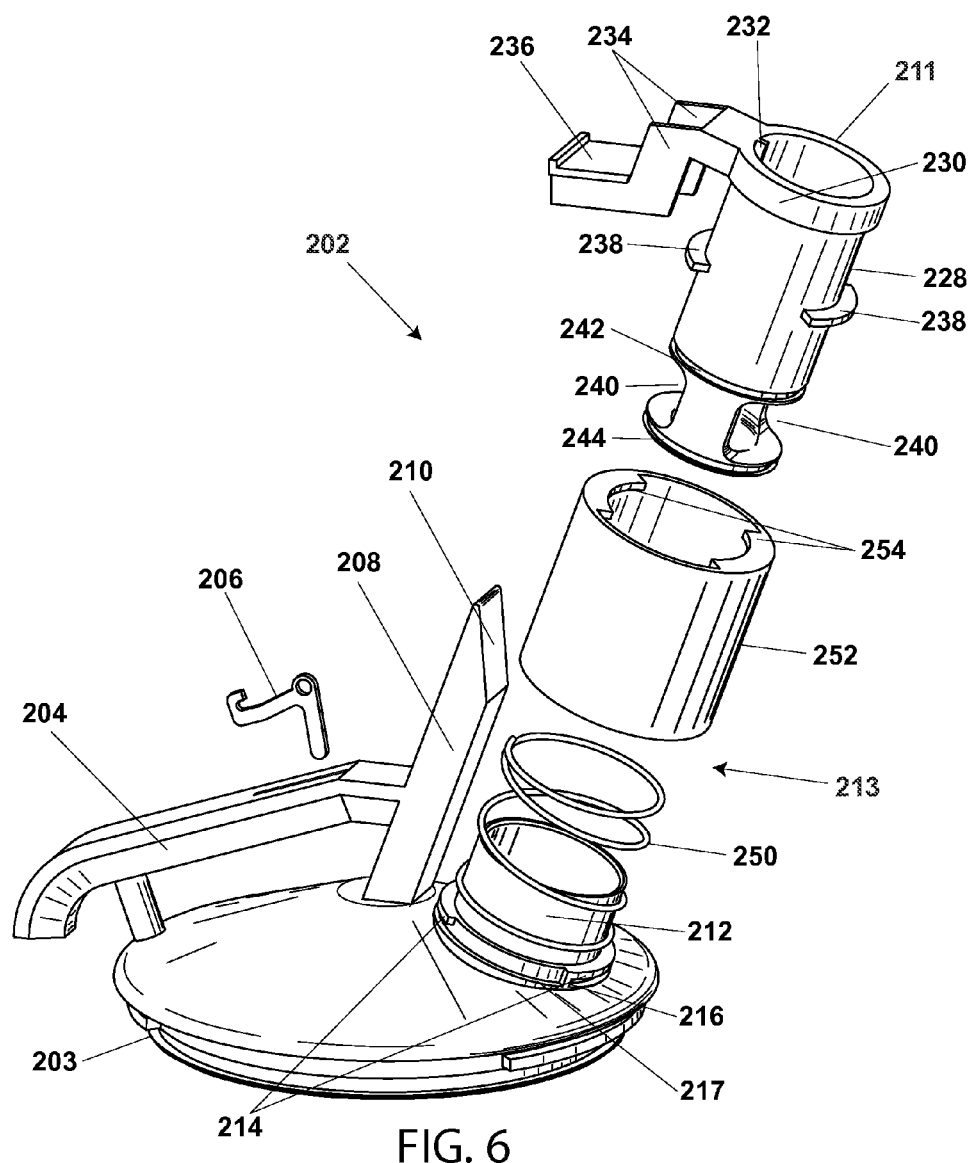
FIG. 6 is an exploded perspective view of the front side of the lid assembly of the reservoir of FIG. 2.

FIG. 6 is an exploded view of the reservoir lid assembly 202 showing the lid cover 203, spout assembly 213 and components of the spout valve assembly 211. Integral to lid cover 203 is a spout 212. The base of spout 212 incorporates two interlock ribs 214 and two interlock rib stops 216 positioned 180° apart around the outer circumference of the spout. Construction of the cylindrical spout valve tube 228 includes the handle collar 230, the handle sides 234, two stop shoulders 238, and two valve ports 240. Each of the said shoulders, and each of the said ports are positioned 180° apart around the outer circumference of the tube. The collar 230 incorporates guide key 232. Tube construction also includes upper and lower O-ring grooves 242 and 244 which, as shown in FIG. 7, retain O-rings 246 and 248 respectively. The tubular retainer collar 252 incorporates, at each end, a set of two interlock ribs 254 positioned 180° apart around the inside of the collar. The two sets of ribs are concentrically aligned with each other.

FIG. 6 shows the fully assembled reservoir 200 including reservoir cup 256 and lid assembly 202. Lid assembly 202 is shown in the closed position, i.e., with spout assembly 213 and spout valve assembly in the closed (normal) position. The spout assembly and spout valve assembly are biased towards the closed position by a tensioning mechanism, for example, as shown spout valve assembly is held in this position by the expansion force of spring 250. The bottom end of the spring rests on the top surface of interlock ribs 214, and the top end of the spring seats against the undersides of the tube stop shoulders 238. Upward travel of the tube is limited by shoulder stops 238 abutting against interlock ribs 254 at the top of the collar. In this position, the tube ports 240 are covered by the spout wall, the O-ring 248 forms a seal between the inner spout wall and the base of the valve tube, and fluid flow between reservoir cup 256 and spout 212 is blocked.

FIG. 7A shows lid assembly 202 in the open position, i.e., spout valve assembly 211 in the open (in use) position. Valve tube 228 is moved into this position via downward manual pressure on the handle thumb grip 236. Downward travel of the tube is limited by the handle collar 230 seating against the top rim of the spout 212. In this position, the tube ports 240 are fully exposed below the underside of the lid, and fluid flow between reservoir cup 256 and the spout tube is enabled. O-ring 246 prevents leakage between the tube and spout inner walls when the Reservoir is up-ended with lid assembly 202 in the open position.

Figure 10:
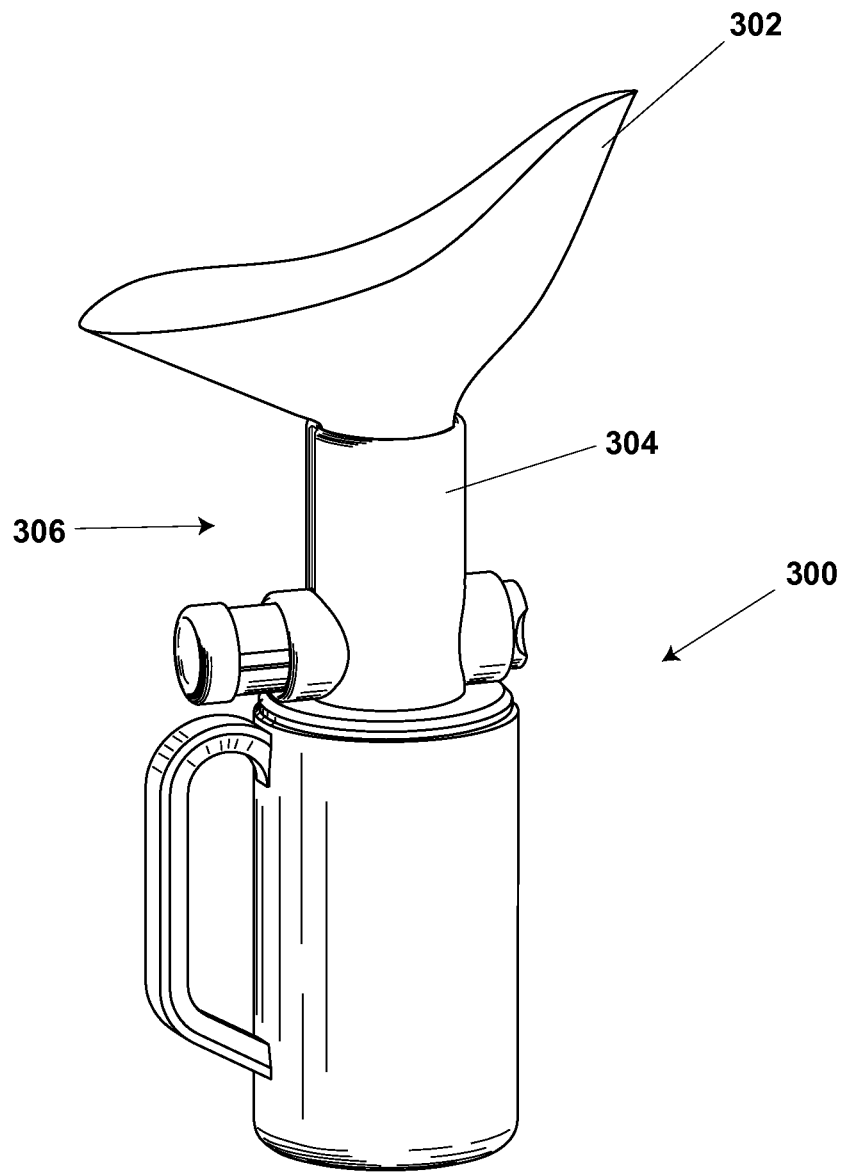
FIG. 10 is a perspective view of another example of a handheld urinal having a female adapted piece attached.

As described herein, the urinal is intended for male use. However it can be easily fitted with a commercially available female adapter. For example, as shown in FIG. 10, a handheld urinal 300 is provided with a female adapter 302 that is inserted into and fitted to an upper section 304 of a neck assembly 306.

Operation

The inventive subject matter also contemplates methods of collecting urine with a portable urinal system. In some embodiments, the method includes the steps of providing a portable urinal system as described above and positioning the handheld urinal to receive urine from the urethral opening of a user, releasing urine into the neck assembly while opening the valve assembly and allowing urine to collect into the urinal cup, closing the valve assembly after urination, coupling the neck assembly of the handheld urinal to the lid assembly of the reservoir, and transferring urine collected in the urinal cup to the reservoir cup by opening both the neck valve assembly and the lid assembly such that urine collected in the urinal cup drains into the reservoir cup.

Referring to FIG. 3, in order to secure urinal neck assembly 102 to urinal cup 160, neck assembly 102 is first rotated 90° counterclockwise from the position shown such that the neck interlock ribs 154 are concentrically offset from the cup interlock ribs 164. It is then inserted into urinal cup 160 until the neck seat 152 is abutted against the cup shoulder 162. Neck assembly 102 is then rotated 90° clockwise with the neck interlock ribs 154 sliding beneath the cup interlock ribs 164 until the two sets of ribs are interleaved and concentrically aligned, and the neck ribs are seated against the rib stops 166. Removal of neck assembly 102 from urinal cup 160 is accomplished by performing the above steps in reverse order.

With urinal neck and valve parts aligned as shown in FIGS. 3B and 3C, the urinal sliding valve is assembled by first inserting the valve plug 126 into the valve sleeve 112 such that lateral grooves 128 engage guide pins 114 on either side of the sleeve. Next the plunger 116 is rotated 90° counterclockwise from the position shown such that the starter grooves 118 line up with the guide pins 114, and the plunger is inserted into the valve sleeve 112 as far as it will go. At this point, the guide pins are aligned with radial guide grooves 120, and the plunger is rotated 90° clockwise until the guide pins align with lateral guide grooves 122. The spring 136 is then inserted into the other end of the sleeve and into plug recess 134. Finally the spring retainer cap 138 is rotated counterclockwise from the position shown such that starter grooves 142 line up with guide pins 114, and the outside end of the spring is abutted against retainer shoulder 140. The cap is then inserted into valve sleeve 112 as far as it will go, and with the guide pins aligned with radial guide grooves 144, the cap is rotated clockwise as far as it will go. Disassembly of the sliding valve is accomplished by performing the above steps in reverse order. To facilitate assembly/disassembly, the plunger, plug, spring, and spring retainer cap are geometrically symmetrical about their respective cylindrical axes.

Referring to FIG. 5, in order to secure reservoir lid 203 to reservoir cup 256, the lid is first rotated 90° counterclockwise from the position shown such that the lid interlock ribs 220 are concentrically offset from the cup interlock ribs 260. It is then inserted into reservoir cup 256 until the lid seat 218 is abutted against the cup shoulder 258. Lid 203 is then rotated 90° clockwise with the lid interlock ribs 220 sliding beneath the cup interlock ribs 260 until the two sets of ribs are interleaved and concentrically aligned, and the neck ribs are seated against the rib stops 262. Removal of lid 203 from reservoir cup 256 is accomplished by performing the above steps in reverse order.

Referring to FIG. 6, the reservoir spout valve is assembled by sliding spring 250 over spout 212 such that the bottom end of the spring is abutted against the top surfaces of spout interlock ribs 214. The spring retainer collar 252 is then rotated 90° counterclockwise from the position shown such that the two sets (top and bottom) of collar interlock ribs 254 are concentrically offset from spout interlock ribs 214. The retainer collar is then slid over spring 250 until the lower interlock ribs of the retainer collar are abutted against the spout base 217. At this point, the retainer collar upper interlock ribs 254 are concentrically offset from the valve tube stop shoulders 238, and the valve tube 228 can be inserted into the spout such that the tube handle sides 234 straddle the guide pillar 208. The tube is inserted until the bottom sides of the stop shoulders 238 are abutted against the top end of spring 250, and the top sides of the stop shoulders are below the bottom sides of collar upper interlock ribs 254. At this point the spring retainer collar is rotated 90° clockwise with the collar lower interlock ribs sliding beneath the spout interlock ribs 214 until the two sets of ribs are interleaved and concentrically aligned, and the collar lower interlock ribs are abutted against rib stops 216. Disassembly of the spout valve assembly is accomplished by performing the above steps in reverse order.

At the time of typical use, the urinal shown in FIG. 1 is held by grasping handle 170 with the fingers of either hand. Applying thumb pressure to plunger 116 opens the plug valve, and urine that is discharged into inlet funnel 104 is allowed to flow into cup 160 (FIGS. 4 and 4A). When thumb pressure is released, spring 136 forces the sliding valve into the fail-safe position (FIG. 4), and the urine is securely contained within the cup.

Referring to FIG. 8, in order to transfer the contents of the urinal into the reservoir cup, the urinal is first inverted, and the urinal neck assembly 102 is then inserted into spout valve tube 228 such that guide groove 108 engages guide key 232. The urinal neck assembly and spout valve assembly 211 are thereby aligned so that when the urinal valve sleeve 112 is abutted against collar 230, the urinal valve plunger 116 will be in contact with reservoir pillar wedge 210. From this point, as the urinal is pressed downward, the spout valve tube will also be pressed downward to its open position, and as the plunger slides against the pillar wedge, the plunger will be depressed inward to its valve open position. The urinal sliding valve and the reservoir spout valve assembly will therefore simultaneously move to their fully open positions as shown in FIG. 8A, and the contents of the urinal cup 160 will drain through the urinal funnel 148 and eventually into the reservoir cup 256.

Figure 9:
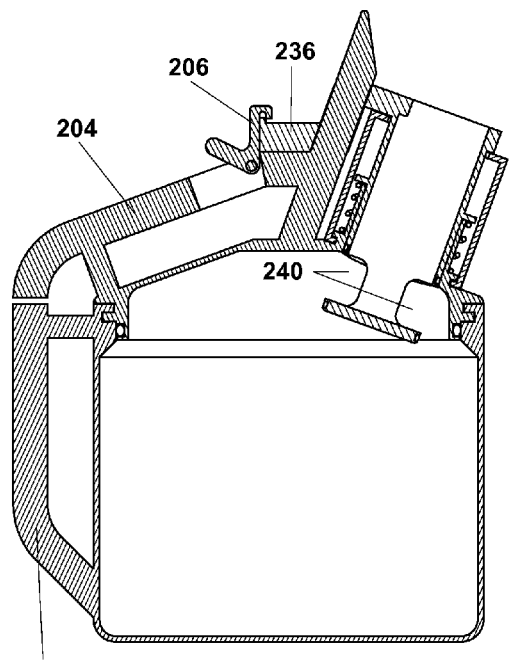
FIG. 9 is a cross-sectional side view of the reservoir showing the latch in a position holding the spout valve assembly open.
Figure 9A:
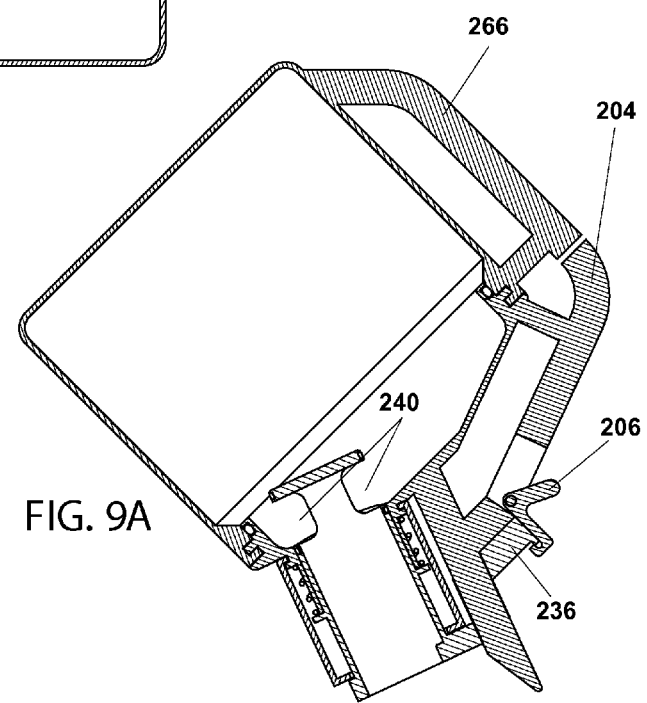
FIG. 9A is a cross-sectional side view of the reservoir showing the reservoir tipped into the pouring position and the spout valve assembly in the open position.

To empty the contents of the reservoir cup, the spout handle thumb grip 236 is first pressed down as far as it will go fully opening the spout valve as shown in FIG. 9. The handle latch 206 can then be optionally flipped into the position shown to hold the spout valve open. With the use of lid handle 204 and/or cup handle 266, the reservoir is then tipped into the pouring position as shown in FIG. 9A allowing the cup contents to drain through the spout tube. The relative positioning of the tube ports 240 is such that as the reservoir is tipped, liquid will flow out through the lower port, and displacement air will flow in through the upper port. The liquid outflow through the spout valve tube will therefore occur with minimal turbulence and splashing.

According to certain embodiments, the portable urinal systems described herein can be incorporated into the cab of a tractor unit used to tow semi-trailers. More specifically the reservoir can be hidden underneath seats, beds, or incorporated into cabinetry within the tractor unit, such as in the sleeper portion of the tractor unit. Thus, tractor units housing a portable urinal system within them are expressly contemplated herein, these embodiments expressly include tractor units having storage space configured to hide and hold the reservoir, and preferably the handheld urinal as well.

In the embodiments shown, all parts are manufactured from high-impact injection molded plastic, with the exception of rubber gaskets and metal springs. For example a stain resistant injection molded plastic. Valve part surfaces that are subject to frictional wear may be made of a nylon type plastic, for example. In other embodiments, parts may be made of any suitable materials, for example stainless steel. However, the system lacks an elongated corrugated connection between the urinal neck assembly and the lid assembly of the reservoir.

The various embodiments described above are provided by way of illustration only and should not be construed to limit the claims attached hereto. Those skilled in the art will readily recognize various modifications and changes that could be made without following the example embodiments and applications illustrated and described herein, and without departing from the true spirit and scope of the following claims.

What is claimed is:

1. A portable urinal system comprising:
a handheld urinal comprising
a neck assembly configured to receive urine from the urethral opening of a user and including a user operated neck valve assembly that when in a normal closed position prevents urine flow through the neck assembly, and when opened by a user permits urine to flow through the neck assembly,
a urinal cup coupled to the neck assembly so that upon use of the urinal and opening of the neck valve assembly by the user, urine flows through the neck assembly into the urinal cup;
a reservoir having a larger volume than the urinal cup comprising
a lid assembly including a substantially rigid spout assembly configured to receive the neck assembly of the urinal such that the configuration of the neck assembly inserted into the spout assembly prevents spillage of urine transferred from the urinal to the reservoir, and
a reservoir cup configured to store urine received from the urinal via the spout assembly.

2. The system of claim 1, wherein the system lacks an elongated corrugated connection between the urinal neck assembly and the lid assembly of the reservoir.

3. The system of claim 1, wherein the neck assembly is substantially rigid.

4. The system of claim 1, wherein the lid assembly comprises a spout valve assembly associated with the spout assembly and wherein the spout valve assembly is operated by coupling the urinal to the reservoir and by applying manual pressure on the urinal towards the reservoir cup causing the neck valve assembly and the spout valve assembly to open simultaneously.

5. The system of claim 1, wherein the neck valve assembly comprises a sleeve housing a valve plunger, the valve plunger being biased to a valve closed position.

6. The system of claim 1, wherein the neck valve assembly comprises a retainer cap preventing disassembly of the neck valve assembly without turning the retainer cap.

7. The system of claim 1, wherein the urinal is sized in volume to receive about 400 to about 600 ml of urine, and wherein the reservoir is sized in volume to store at least about 1600 to about 6000 ml of urine.

8. The system of claim 1, wherein the urinal neck assembly includes a releasably detachable adapter configured to receive urine from the urethral opening of a female when attached; and allows for the neck assembly to couple to the lid assembly when detached.

9. The system of claim 1, wherein the urinal neck assembly is adapted for male use.

10. The system of claim 1, wherein the neck assembly and urinal cup are releasably coupled.

11. The portable urinal system of claim 1, wherein
the neck assembly has an upper section configured to receive urine from the urethral opening of the user, a middle section having a sleeve which houses a user operated sliding plug valve, and a lower section having an outlet and a plurality of coupling elements, and
the urinal cup coupled to the neck assembly via the plurality of complementary coupling elements.

12. A method of collecting urine with a portable urinal system, the method comprising:
providing a portable urinal system comprising
a handheld urinal comprising
a neck assembly configured to receive urine from the urethral opening of a user and including a user operated neck valve assembly permitting urine to flow through the neck assembly,
a urinal cup coupled to the neck assembly so that upon use of the urinal and operation of the neck valve assembly by the user, urine flows through the neck assembly into the urinal cup;
a reservoir having a larger volume than the urinal cup comprising
a lid assembly including a substantially rigid spout assembly and the lid assembly configured to releasably couple to the neck assembly of the urinal, and
a reservoir cup configured to store urine received from the urinal via the spout assembly;
positioning the handheld urinal to receive urine from the urethral opening of a user;

releasing urine into the neck assembly while opening the valve assembly and allowing urine to collect into the urinal cup;

closing the valve assembly after urination;

coupling the neck assembly of the handheld urinal to the lid assembly of the reservoir;

transferring urine collected in the urinal cup to the reservoir cup by opening both the neck valve assembly and the lid assembly such that urine collected in the urinal cup drains into the reservoir cup.

13. The method of claim 12, wherein the neck valve assembly comprises a sleeve housing a sliding valve plunger, the valve plunger being biased to a valve closed position.

14. The method of claim 12, wherein the portable urinal system lacks an elongated corrugated connection between the urinal neck assembly and the lid assembly of the reservoir.

15. The method of claim 12, wherein the urinal comprises a neck assembly that is substantially rigid.

16. The method of claim 12, wherein the urinal is sized in volume to receive about 400 to about 600 ml of urine, and wherein the reservoir is sized in volume to store at least about 1600 to about 6000 ml of urine.

17. The method of claim 12, wherein the neck assembly includes a releasably detachable adapter configured to receive urine from the urethral opening of a female when attached; and allows for the neck assembly to couple to the lid assembly when detached.

18. The method of claim 12, wherein the neck assembly is adapted for male use.

19. The method of claim 12, wherein the lid assembly comprises a spout valve assembly associated with the spout assembly and wherein the spout valve assembly is operated by coupling the urinal to the reservoir and by applying manual pressure on the urinal towards the reservoir cup causing the neck valve assembly and the spout valve assembly to open simultaneously.

* * * * *